United States Patent
Sun

(10) Patent No.: US 8,715,307 B2
(45) Date of Patent: May 6, 2014

(54) DEVICE FOR PERFORMING AN INCISION

(75) Inventor: Jian Ping Sun, Singapore (SG)

(73) Assignee: Medipurpose Pte Ltd, Singapore (SG)

(*) Notice: Subject to any disclaimer, the term of this patent is extended or adjusted under 35 U.S.C. 154(b) by 187 days.

(21) Appl. No.: 12/517,002

(22) PCT Filed: Dec. 1, 2006

(86) PCT No.: PCT/SG2006/000375
§ 371 (c)(1),
(2), (4) Date: May 29, 2009

(87) PCT Pub. No.: WO2008/066491
PCT Pub. Date: Jun. 5, 2008

(65) Prior Publication Data
US 2010/0076472 A1    Mar. 25, 2010

(51) Int. Cl.
*A61B 17/32* (2006.01)
(52) U.S. Cl.
USPC .......................................................... 606/182
(58) Field of Classification Search
USPC ........................................ 606/181, 182, 167
See application file for complete search history.

(56) References Cited

U.S. PATENT DOCUMENTS

| | | | | |
|---|---|---|---|---|
| 4,628,929 A | * | 12/1986 | Intengan et al. | 606/182 |
| 4,643,189 A | * | 2/1987 | Mintz | 606/182 |
| 5,314,441 A | * | 5/1994 | Cusack et al. | 606/182 |
| 5,527,333 A | * | 6/1996 | Nikkels et al. | 606/182 |

(Continued)

FOREIGN PATENT DOCUMENTS

| | | |
|---|---|---|
| DE | 102004045043 | 4/2006 |
| EP | 0747006 | 12/1996 |

(Continued)

OTHER PUBLICATIONS

Supplementary European Search Report dated Jan. 12, 2010 for related European Application No. EP06824646.

(Continued)

*Primary Examiner* — Kathleen Holwerda
*Assistant Examiner* — Sarah Simpson
(74) *Attorney, Agent, or Firm* — Troutman Sanders LLP; Ryan A. Schneider; Benjamin C. Wiles

(57) ABSTRACT

The present invention relates to a device for performing an incision in a region of interest of a patient, said device including a blade portion for providing the incision, said blade attached to a biasing means to enact a vertical force on said blade so that the blade is biased in a retracted position, a triggering means for activating the blade to move from a previously retained pre-operating position, to an operating position where the blade contacts a region of interest of the patient thereby performing an incision, and to a post operating position, a guide means to guide a path of the blade as it moves in an operating position said blade portion adapted to engage said guide means when in an operating position, so that a path of the blade in an operating position is guided, the device further including a housing to house said device, said housing having an elongate slot at one end, where in an operating position, the blade extends therethrough said slot, and in a pre and post operating position, the blade does not extend therethrough said slot, wherein the blade, biasing means and the triggering means are integral to one another, forming a plate.

11 Claims, 12 Drawing Sheets

(56) References Cited

U.S. PATENT DOCUMENTS

| | | | |
|---|---|---|---|
| 5,782,852 A * | 7/1998 | Foggia et al. | 606/182 |
| 5,797,940 A | 8/1998 | Mawhirt et al. | |
| 5,951,582 A | 9/1999 | Thorne et al. | |
| 6,042,595 A * | 3/2000 | Morita | 606/181 |
| 6,221,089 B1 * | 4/2001 | Mawhirt | 606/181 |

FOREIGN PATENT DOCUMENTS

| | | |
|---|---|---|
| JP | 64042010 | 2/1989 |
| JP | 04261645 | 9/1992 |
| JP | 06007329 | 1/1994 |
| JP | 2000245715 | 9/2000 |
| JP | 2002045351 | 2/2002 |
| JP | 2002143131 | 5/2002 |
| JP | 2002516147 | 6/2002 |
| JP | 2004344292 | 12/2004 |
| JP | 2005046628 | 2/2005 |
| JP | 2005169003 | 6/2005 |
| JP | 2005192713 | 7/2005 |
| WO | 2004091401 | 10/2004 |
| WO | 2004103178 | 12/2004 |
| WO | 2005102166 | 11/2005 |
| WO | 2006058654 | 6/2006 |
| WO | 2006110572 | 10/2006 |

OTHER PUBLICATIONS

Office Action issued by the Japanese Patent Office dated Mar. 28, 2012 for related Application No. JP2009-539217.
Decision of Patent Grant dated Jul. 10, 2012 for related Japanese Patent Application No. 2009-539217.
Decision of Rejection dated Aug. 2, 2012 for related Chinese Patent Application No. 200680056492.X.
Popov, Egor P., "Engineering Mechanics of Solids", Princeton Hall, 2nd Edition, p. 711, Aug. 20, 1998.

* cited by examiner

DEVICE FOR PERFORMING AN INCISION

BENEFIT CLAIMS

This application is a U.S. National Stage of International Application No. PCT/SG2006/000375, filed 1 Dec. 2006.

FIELD OF THE INVENTION

The present invention relates to a device for performing an incision for the collection of a blood sample, and more particularly, to a device for performing an incision on an individual's heel for diagnostic purposes.

BACKGROUND OF THE INVENTION

The heel stick procedure to puncture a newborn's heel to obtain a blood sample is widely practiced for babies aged 6 months and below. The blood samples obtained from this procedure are sent for diagnostic processing predominantly for screening of diseases, for example hypothyroidism, PKV (or phenylketonuria), galactosemia, sickle cell disease, HIV infection, etc. The advantages observed from the screening of these diseases are widely known and will not be discussed.

As the blood samples are to be obtained from infants, any incision should be made with minimum discomfort to the infant and therefore, issues like consistency in the type of incision or puncture, having a minimal depth of cut whilst still being able to obtain an adequate volume of blood for sampling to be performed, are critical. On the other hand, the device has to have ease of use and have repeatability of results.

For hygiene purposes, these devices are made for single usage and therefore, low cost of manufacturing is also a consideration so that a cheap and reliable device may be produced.

For the purposes of safety, the blades of the devices are usually stowed away to prevent cross contamination during disposal.

There are presently several lancet devices available in the market.

Some of these lancet devices produce an incision by way of a substantially downward thrust on a patient causing a puncture wound or a substantially vertical incision, others cause an incision profile by way of a slicing action causing a substantially lateral incision profile.

In the lancet devices of the prior art, the incision is activated by a trigger mechanism, which impacts a blade or blade-carrying portion to cause the incision to occur.

The problem with this type of activation is that the incision is activated indirectly. Possible problems caused by this indirect activation mechanism would be the possibility of the trigger mechanism being jammed or broken and the inconsistency of the impact force resulting in an inconsistent incision.

It is an object of the present invention to alleviate one or all of the above problems.

SUMMARY OF THE INVENTION

According to a first embodiment of the invention, there is provided a device for performing an incision in a region of interest of a patient, said device including a blade portion for providing the incision, said blade attached to a biasing means to enact a vertical force on said blade so that the blade is biased in a retracted position, a triggering means for activating the blade to move from a previously retained preoperating position, to an operating position where the blade contacts a region of interest of the patient thereby performing an incision, a guide means to guide a path of the blade as it moves in an operating position said blade portion adapted to engage said guide means when in an operating position, so that a path of the blade in an operating position is guided, the device further including a housing to house said device, said housing having an elongate slot at one end, where in an operating position, the blade extends therethrough said slot, and in a pre-operating position, the blade does not extend therethrough said slot, wherein the blade, biasing means and the triggering means are integral to one another, forming a plate.

Preferably, the guide means is a cam having accurate profile having a curved valley portion of a substantially central portion of the profile.

Still preferably, when the triggering means is depressed, the blade, biasing means and triggering means rotate about a point on the housing.

In a second embodiment, the device further includes a stopping means to maintain the blade in a post-operating position, where the blade does not contact the patient.

Preferably, the stopping means is an extended lip extending from a periphery of the housing, extended to project a portion of the triggering means so that the blade and the biasing means are retained in a post-operating system.

Still preferably, the stopping means further includes an extended finger, extending from the triggering means, to abut the extended lip so as to stop a rotation of the device.

In a third embodiment, the device further includes a retaining means to maintain the blade in a pre-operating position, where the blade does not contact the patient.

Preferably, the retaining means is a rotatable plate, rotatable about an edge of the housing to contact the triggering means so that it may not be depressed.

In a variation, the rotatable plate is a sheath.

In a fourth embodiment, the device further includes a cover adaptable to be fixed over at least the triggering means so that the triggering means will not be accidentally activated.

DESCRIPTION OF THE FIGURES

In order that the present invention might be more fully understood, embodiments of the invention will be described, by way of example only, with reference to the accompanying drawings, in which.

In each of the aspects and variations, the same reference numerals have been used for similar components, merely for ease of understanding the specification.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill of the art that the present invention may be practiced without these specific details. In other instances, well known methods, procedures, components, and features have not been described in detail as not to unnecessarily obscure aspects of the present invention.

Figure 1:
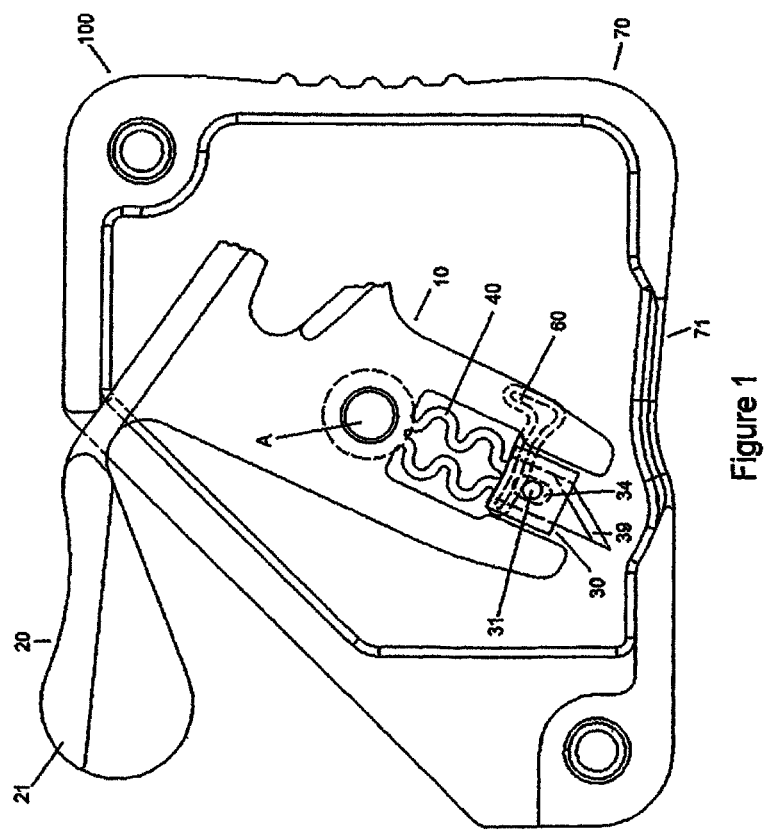
FIG. 1 shows a first embodiment of the invention in a pre-operating position.

As shown in FIG. 1, the present invention relates to a device 100 for performing an incision in a region of interest of a patient of a first embodiment. The device 100 is placed directly on, or proximal to a region of interest of a patient.

The device 100 includes a plate 10 wherein a triggering means 20, a blade holder 30 where a biasing means 40 resides. The biasing means 40 is in communication with the blade holder 30 and enacts an inward force on the blade holder 30, so that when a blade 39 is engaged with the blade holder 30, blade 39 is biased towards a retracted position. These 3 elements being integral to one another, the force relayed to the blade holder by the triggering means will be consistent and predictable, as the force affected on the triggering means will be translated to the blade holder and blade directly. The triggering means 20 activates the plate 10 to move from a pre-operating position, where the blade does not contact or cause an incision on a region of interest of a patient, to an operating position, where the blade contacts or causes an incision on a region of interest of a patient, and finally to a post-operating position. FIG. 1 shows a first embodiment of the invention in a pre-operating position.

Essentially, as the triggering means 20 and blade holder 30 are provided in or otherwise integral to the plate 10, a force enacted on the triggering means 20 will consequently enact on the blade holder 30. A guide means 60 is also provided on the blade holder 30 to guide a path of the blade engaged in the blade holder when the device 100 is in an operating position so as to produce a consistent incision on a region of interest of a patient when the device is in an operating position.

In the embodiments, the surface profile of the guide means 60 has a cam having an arcuate profile with a curved valley portion at a substantially central portion of the profile, or in a skewed 'V' profile, however, it is envisioned that the guide means may be of any other profile to effect a desired incision profile on a patient.

The blade further includes an engagement means in the form of an aperture 34 complementary to an engagement protrusion 31 of the blade holder 30, to engage the blade 39 to the blade holder 30. The blade has at least an aperture 34 dimensioned to engage with the engagement protrusion 31 of the blade holder 30. The guide means 60 is in the form of a guide protrusion on the blade holder 30 on an opposed side to the inward facing engagement protrusion 31. In FIG. 1, the engagement protrusion and guide protrusion are integral as it extends inward to outward of the blade holder 30.

The guide protrusion is positioned at a pre-determined location along the blade holder 30 where it contacts the surface profile of the guide means 60. The pre-determined location of the guide protrusion is such that the biasing means 40 in communication with the blade holder and the blade, is held at a displacement from its equilibrium position so that the position of the blade is held in tension. The pre-determined location of the protrusion 31 and aperture 34 may be easily calculated by a person skilled in the art and will therefore not be discussed. When the triggering means 20 is activated or specifically, the triggering means is depressed, the plate is moved to an operating position by a substantially lateral force. By virtue of the biasing means, the guide protrusion 31 is in constant contact with a surface profile of the cam. Therefore when in an operating position, where a force is effected by the triggering means, the protrusion 31 traverses the surface profile of the cam. Consequently, the path of the blade follows the surface profile of the cam. Therefore, the surface profile of the cam determines the type, or rather, the profile of incision to be effected on a region of interest of a patient.

The device further includes a housing 70 wherein the plate 10 substantially resides. The plate 10 is pivotally connected about a point A to allow the plate 10 to rotate about a point. When in operating position, the plate 10 rotates about point A to move from a pre-operating position to a post-operating position when the triggering means 20 is activated.

During the period between the pre-operating and post-operating position, the plate 10 is in an operating position.

The housing 70 includes an elongated slot 71 wherein the blade 39 extends therethrough when in an operating position.

Therefore, the elongated slot 71 is the region along which an incision is made on a region of interest of a patient. As can be appreciated, when in use, the elongated slot is placed over the region of interest of a patient.

Figure 2:
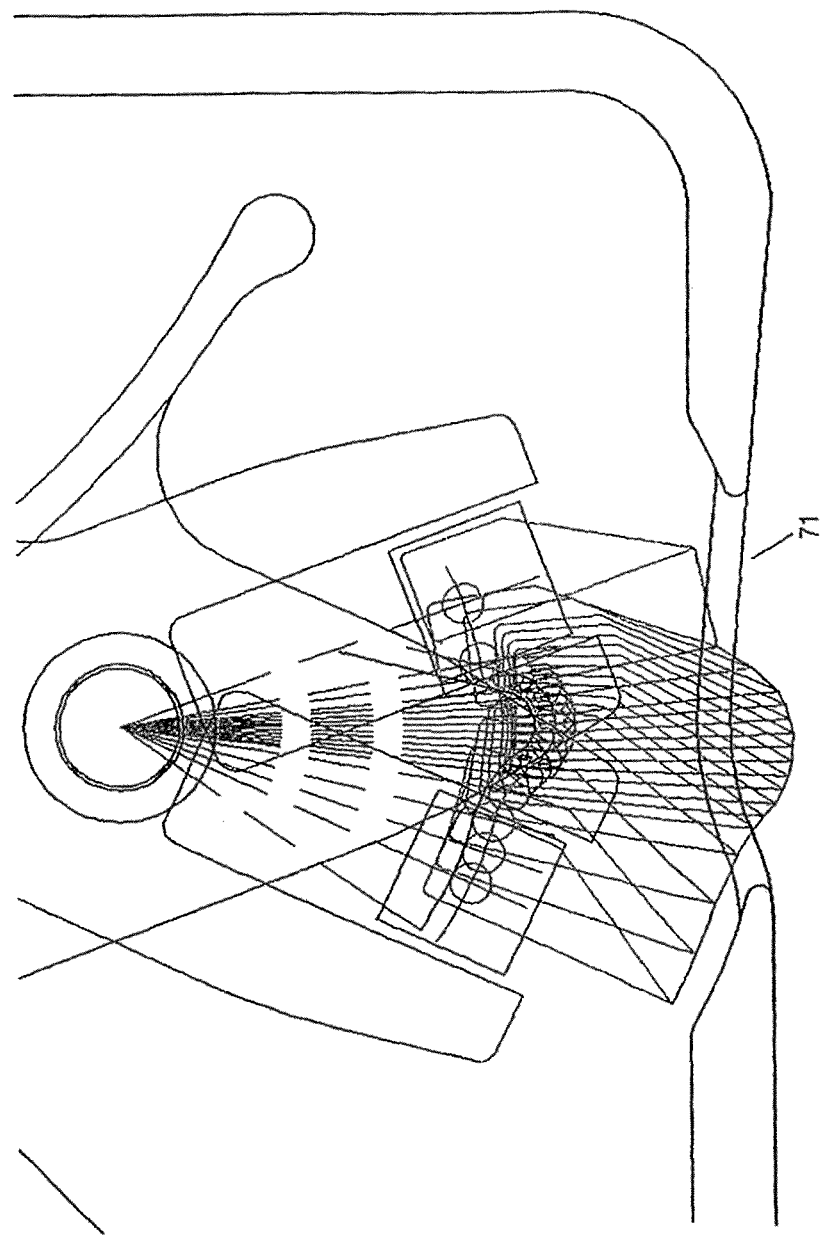
FIG. 2 shows a profile of the incision using a guide means of the present invention.

The position of the elongated slot 71 and the guide means is substantially in alignment with each other, so that the path of the blade, as it extends from the elongated slot 71, is guided and pre-determined. The profile of the incision using the guide means of a surface profile in the exemplary embodiment is shown in FIG. 2. The incision is made by a lateral "slicing action" as opposed to a vertical "stabbing action". Advantageously, the incision action provided by the present device is better than a stab action because the resistance to the cutting edge of the blade being imposed on the skin and tissue is from small to big and then to small. This causes less pain than a stab action does. The width of the incision opening is parabolic, meaning it opens from a narrow to a wider, and ending with a narrow shape of wound. Wounds caused by this type of incision heals easily.

For the purposes of controlling blood volume after an incision, the best shape of incision would be a parabola. Specifically, as the object of the incision is a baby's heel, the depth of the incision should be controlled to a certain range. This is based on a combination of factors being the incision depth, incision opening length and the incision profile area.

Figure 3:
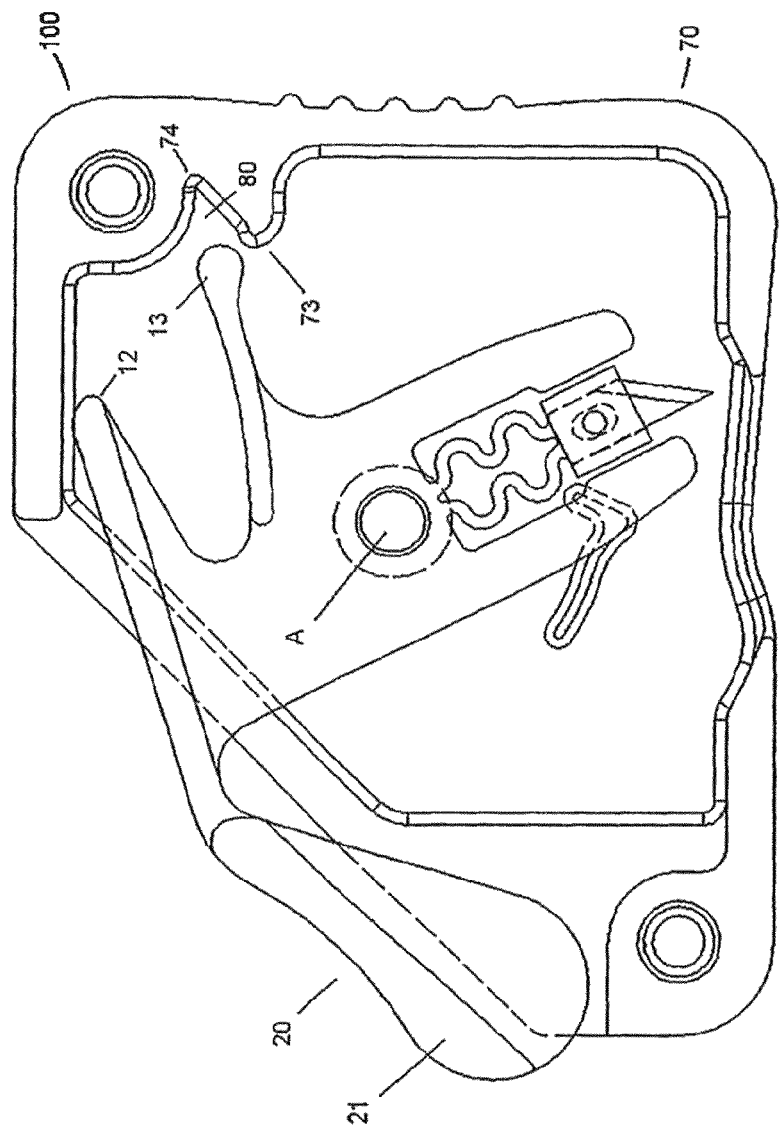
FIG. 3 shows a second embodiment of the invention having a stopping means in a post-operating position.

FIG. 3 shows a second embodiment of the present invention where the device 100 further includes a stopper means 80 to allow the rotation of the plate 10 to come to a stop at a post-operating position. At the post operating position, the blade would be retracted from the elongated slot 71 so that accidental incisions will not be made. The stopper means 80 maintains a post-operating position of the device and in this embodiment, the device 100 is a single-use device.

Figure 4:
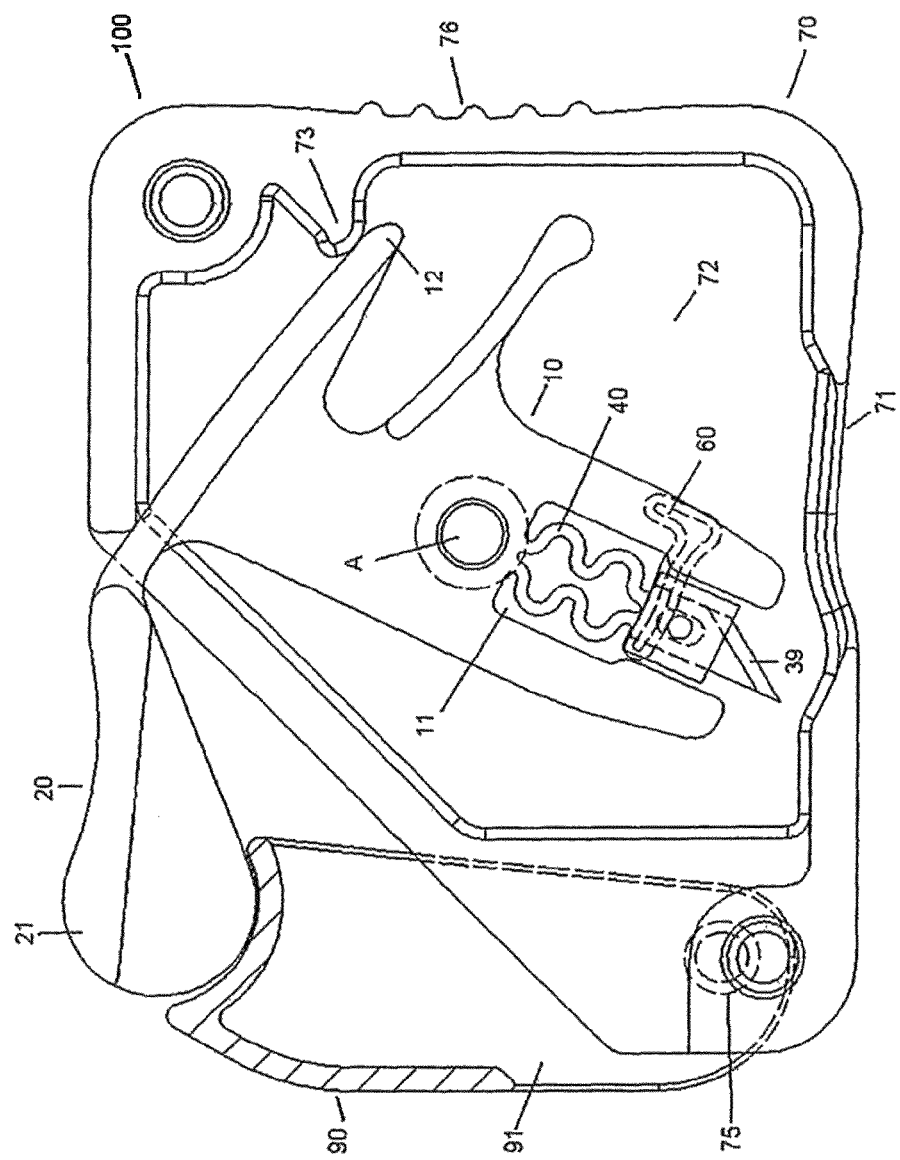
FIG. 4 shows a third embodiment of the invention having a retaining means in the form of a safety catch in a pre-operating position.

FIG. 4 shows a third embodiment of the present invention where the device further includes a retaining means 90 so that the triggering means 20 will not be inadvertently triggered. The retaining means 90 retains the position of the triggering means 20 at a pre-operating position. The retaining means is shown as a rotatable plate 91, rotatable about an edge 75 of the housing to contact the triggering means so that it may not be depressed when the retaining means 90 is in place. When a user wishes to use the device, the rotatable plate 91 is rotated about the edge 75 so that the trigger may be depressed.

In the embodiments, the triggering means 20 and biasing means 40 are formed on the plate 10, the triggering means is in the form of a lever arm 21, which may be depressed downwardly to rotate the plate as a whole about the point of pivot A.

The point of pivot A is formed on an underside 72 of the housing in the form of a hole, the plate having a complementary protrusion is simply depressed into the hole to effect a connection. In this embodiment, the plate 10 is retained onto the protrusion by any known means in such a way that it may still rotate freely about the point of pivot A.

In a variation, the point of pivot A is formed on an underside 72 of the housing in the form of a protrusion, the plate having a complementary hole is simply depressed into the protrusion to effect a connection. In another embodiment, the plate 10 is retained onto the hole by any known means in such a way that it may still rotate freely about the point of pivot A.

The plate 10 has a recessed region 11 wherein the biasing means 40 resides. The biasing means 40 may be any known form of biasing means for example a spring, or any resilient material for example plastic.

The blade 39 may be engaged with the biasing means by any form of adhesion or it may be formed thereon the plate 10.

As seen in FIG. 1, the extension of the finger 12 abuts the extended lip 73 when in a pre-operating position. By depressing the triggering means in the form of a lever arm 21, the force allows the lever arm 21 to overcome the extended lip 73 to rotate about the pivot A and be in an operating position. Advantageously, the force provided by depressing the lever arm 21 will cause the finger 12 to be initially stressed. This stress builds up until such time the extended lip 73 is overcome. Due to the resilience of the plate, the accumulated force will cause the plate 10 to rotate at a high speed. This causes the blade to move quickly and thereby reduce the pain of the patient during the incision.

The stopper means is in the form of a second finger 13 extending from the plate 10. The second finger 13 is dimensioned to be received in a recess 74 formed on an inner periphery of the housing when the device 100 is in a post-operating position. Additionally, at the post operating position, the finger 12 abuts the inner periphery of the housing 70.

Figure 5:
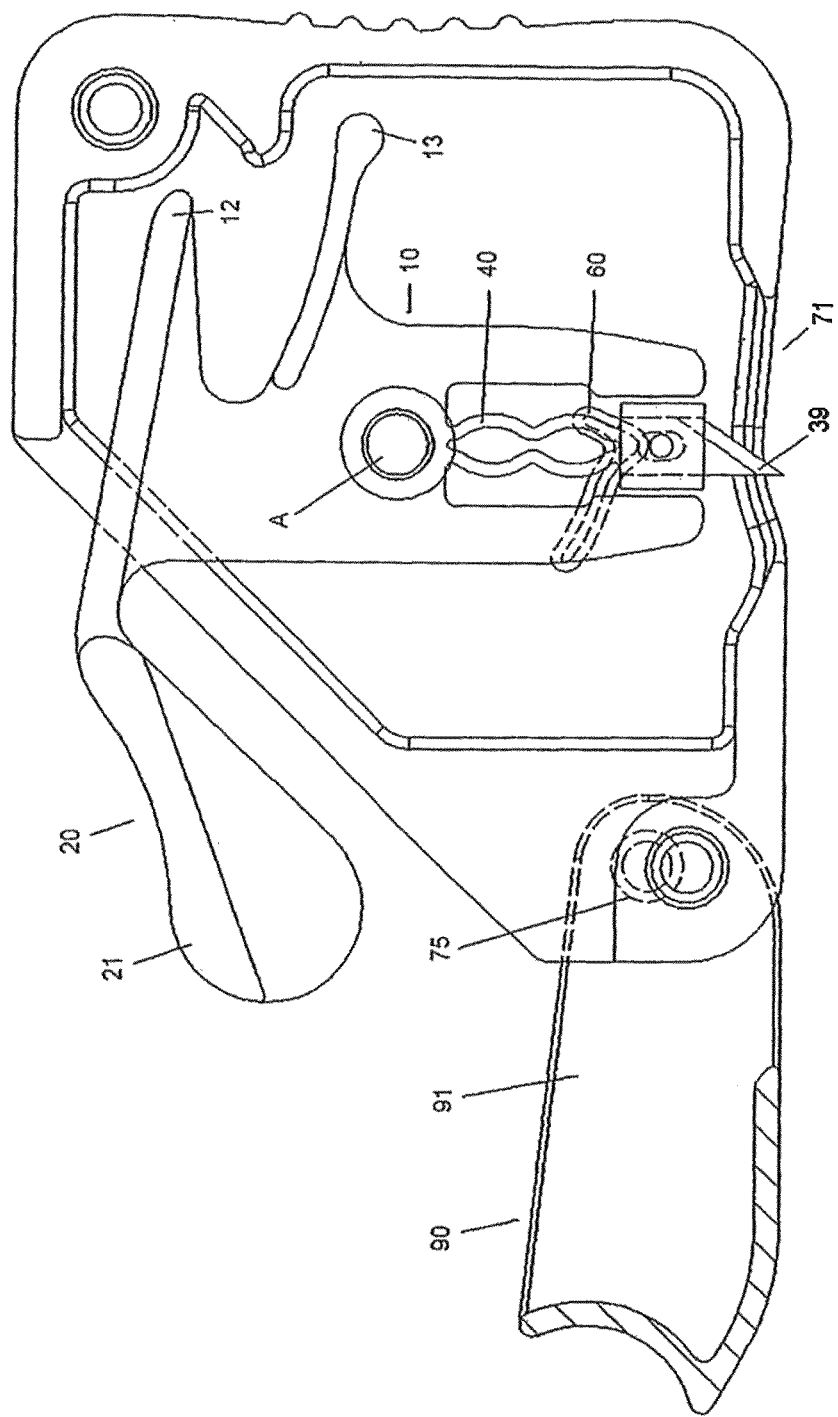
FIG. 5 shows the invention in an operating position.

FIGS. 1 and 4 show the device in a pre-operating position, FIG. 3 shows the device in a post-operating position and FIG. 5 shows the device in an operating position.

Figure 6:
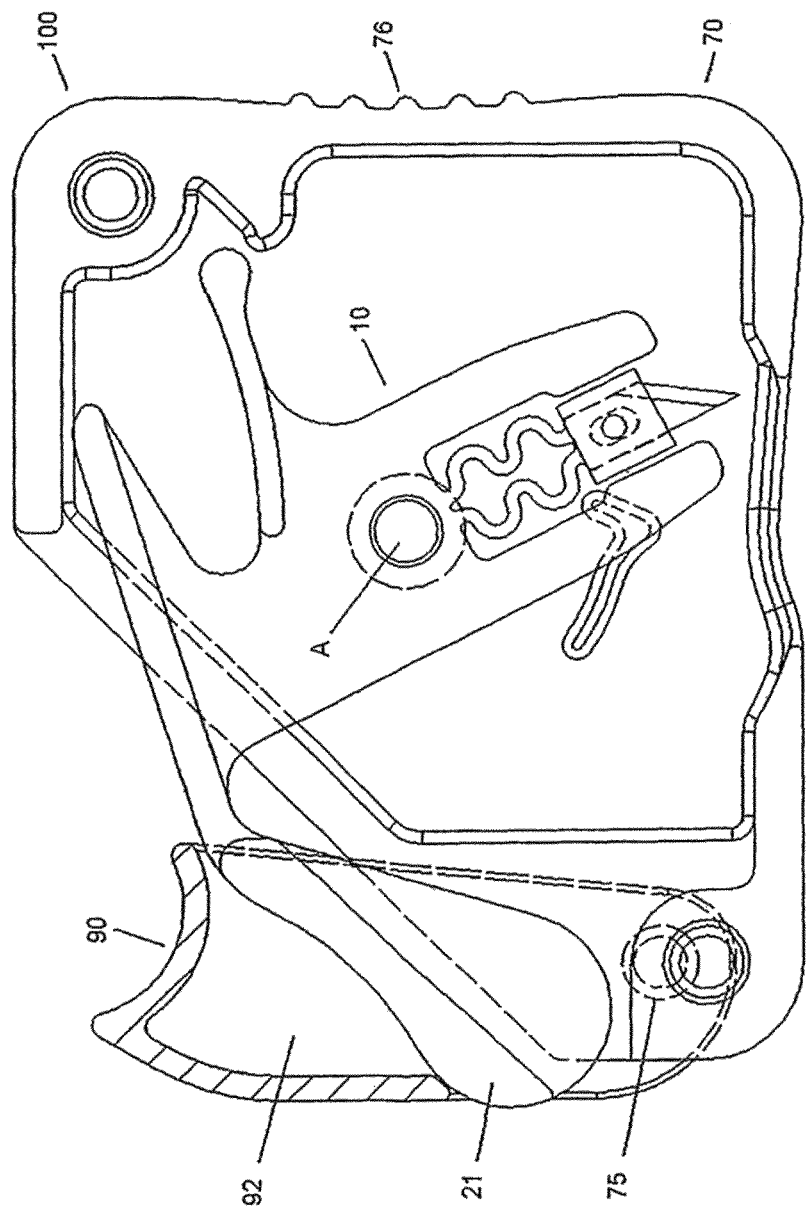
FIG. 6 shows a variation of the retaining means.

FIG. 6 shows a variation of the third embodiment of the device. In this variation, the retaining means 90 is a sheath 92, which allows the triggering means or lever arm 21 to reside therein, when the device has been used. Maintaining the lever arm in the sheath also prevents the blade from moving from a post operating position to an operating position, and makes for easy disposal. The sheath 92 may be held in that position by any known means.

Figure 7:
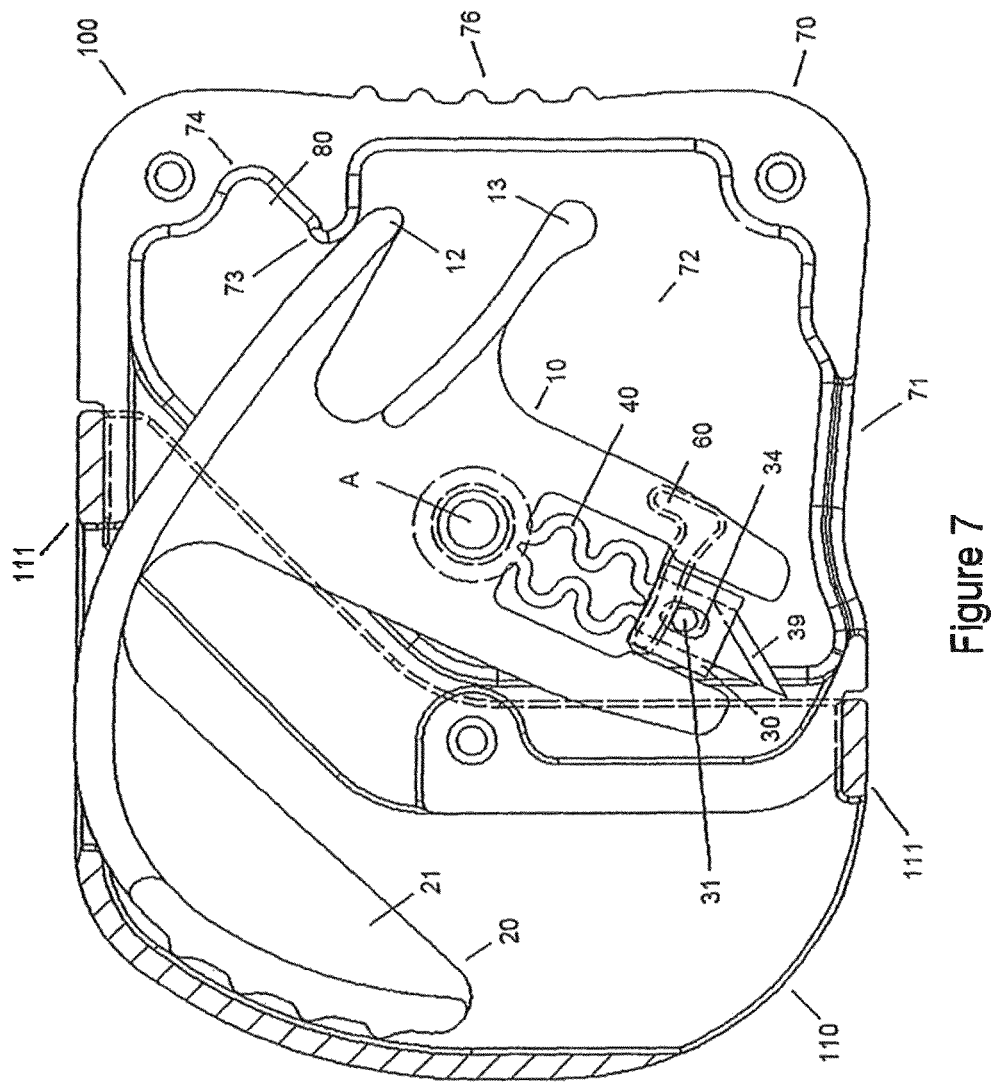
FIG. 7 shows a fourth embodiment of the present invention.

In a fourth embodiment as seen in FIG. 7, the device has a cover 110 placed over the triggering means.

In a variation, the cover 110 is a cap and is affixed to at least two surfaces 111 to the housing of the device to prevent accidental activation of the triggering means. In this variation, the cover may be easily removed, or placed over the triggering means by a user.

In the embodiments, when in used, a user grasps the triggering means 20 preferably with a thumb, and the rest of fingers grasp an opposed end of the housing. To enhance the comfort of a user, the opposed end of the housing is provided with a ribbed or otherwise corrugated surface 76. Additionally, the ribs indicate a correct position where the fingers may rest so that a proper incision may be performed.

In further variations of the embodiments as seen in FIGS. 8 to 12, the shape of the triggering means is curved or otherwise ergonomically shaped to increase the comfort of a user using the device 100.

In these variations, the surface of the triggering means is ribbed or corrugated so that a firm grip may be effected.

Figure 8:
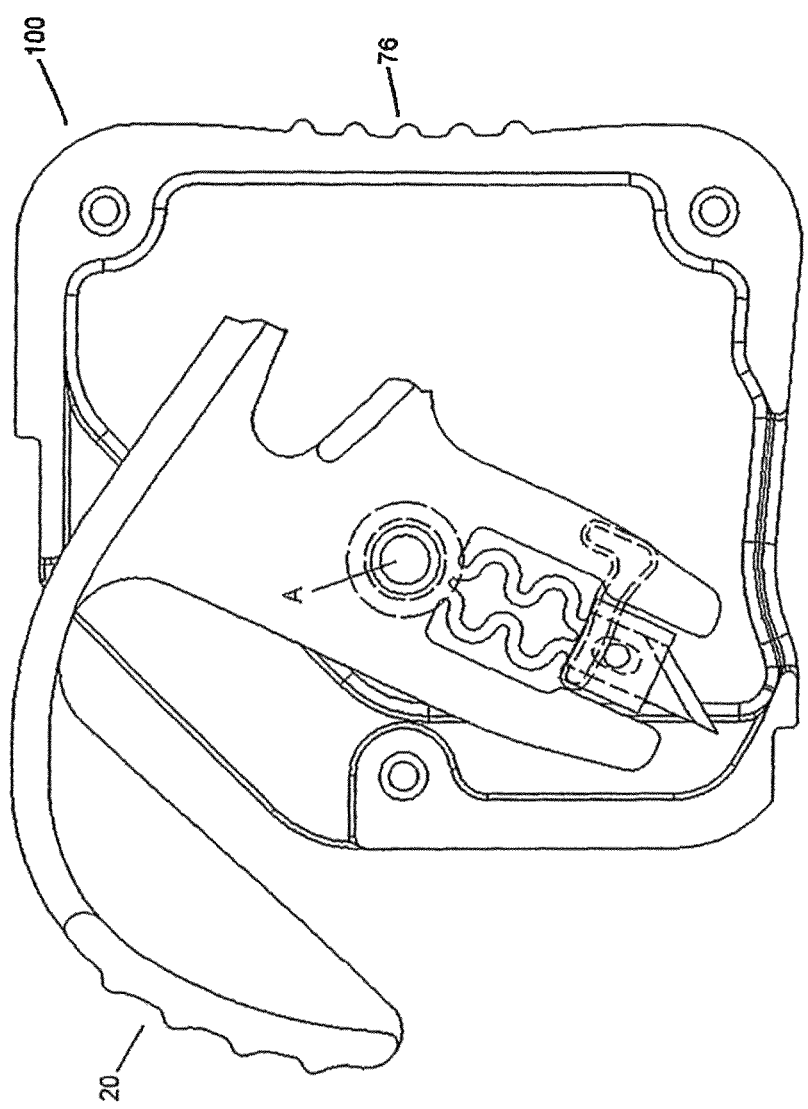
FIG. 8 shows a variation of the first embodiment of the present invention.
Figure 9:
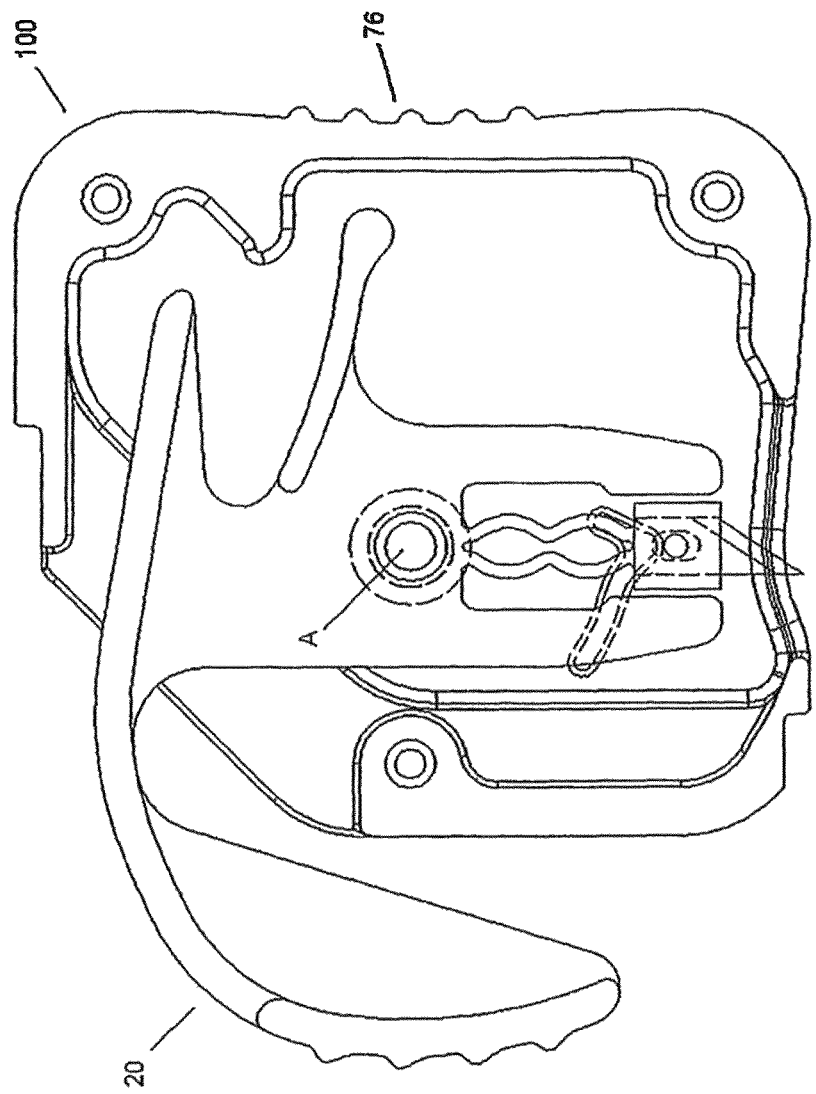
FIG. 9 shows a variation of the second embodiment of the present invention in an operating position.
Figure 10:
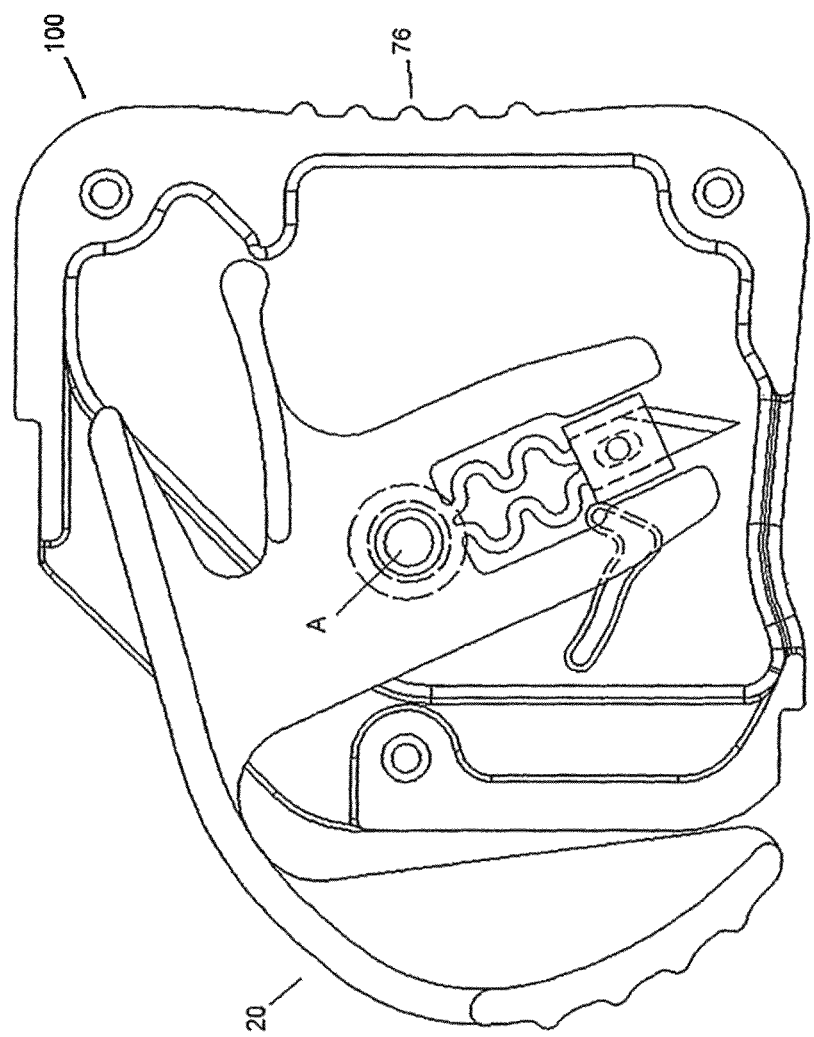
FIG. 10 shows a variation of the second embodiment of the present invention in a post operating position.

In the variation of the first embodiment as shown in FIG. 8, the device is shown in a pre-operating position. In the variation of the second embodiment, as seen in FIGS. 9 and 10. The device is shown in an operating position in FIG. 9, and a post operating position in FIG. 10.

Figure 11:
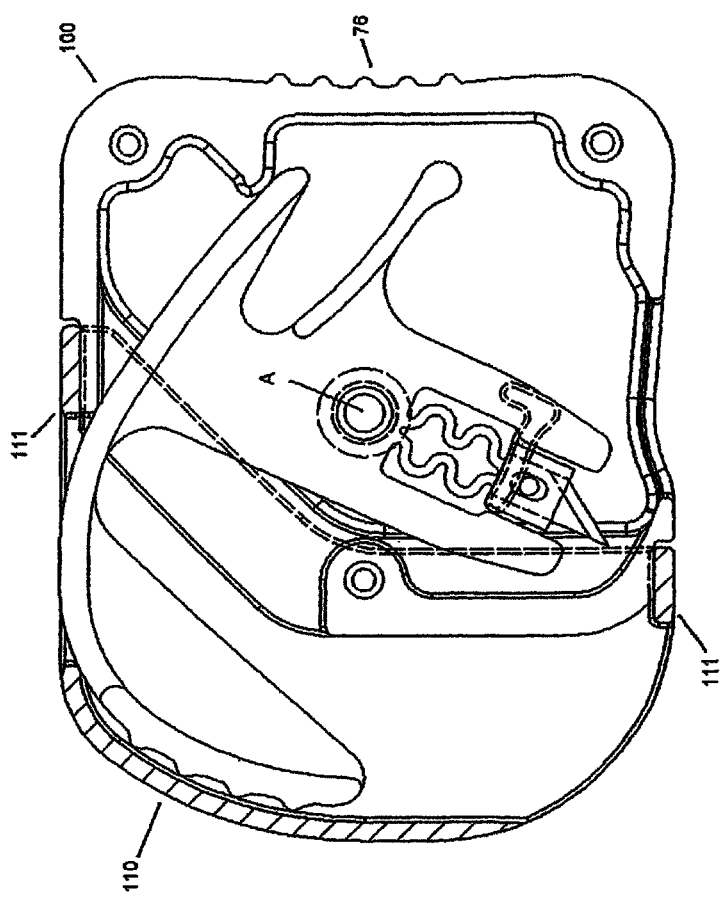
FIG. 11 shows a variation of the fourth embodiment of the present invention in a pre operating position.
Figure 12:
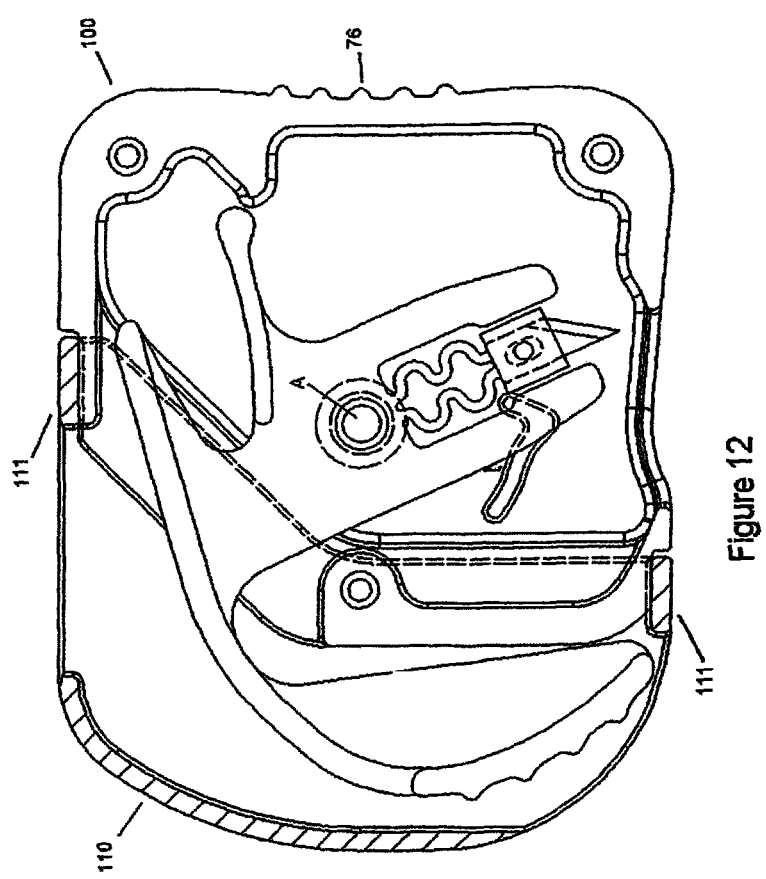
FIG. 12 shows a variation of the fourth embodiment of the present invention in a post operating position.

FIGS. 11 and 12 show a variation of the fourth embodiment of the invention.

The embodiments of the invention have been advanced by way of example only, and modifications are possible within the scope of the invention as defined by the appended claims.

The invention claimed is:

1. A device for performing an incision in a region of interest of a patient, the device comprising:
   a housing having an elongate slot at one end thereof;
   a blade arranged to be biased in a retracted position within the housing in a pre-operating position and a post-operating position;
   a guide having a cam having an arcuate profile having a curved valley portion of a substantially central portion of the profile for guiding the blade through a pre-determined cutting path, and for guiding the blade from the pre-operating position through an operating position to the post-operating position; and
   a plate including:
      a blade holder for holding the blade, the blade holder having a guide protrusion arranged to engage with the guide in the operating position;
      a bias configured to enact an inward force on the blade holder so as to bias the blade towards the retracted position to retain the blade within the housing in the pre-operating position and the post-operating position; and
      a trigger for triggering the blade to extend through the elongate slot in the operating position to make the incision,
   wherein the blade is guided through the pre-determined cutting path of the blade by contact of the guide protrusion with the arcuate profile of the guide to make the incision having a parabolic shape;
   wherein the blade holder is connected to the trigger through the bias and the blade, the bias and the trigger are configured to rotate about a point on the housing when the trigger is depressed, wherein the blade is rotated through the pre-determined cutting path.

2. The device of claim 1 wherein the plate and the trigger comprise a one-piece element.

3. The device of claim 1 further comprising a stop element carried by the plate and engaging the housing for stopping the pivotal movement of the plate at a post-operating position.

4. The device of claim 3, wherein the stop element comprises a second finger extending from the plate, and configured to be received in a recess formed on an inner periphery of the housing so that the blade and the bias are retained in the post-operating position.

5. The device of claim 1 further comprising a retaining element projecting from the plate and engaging a portion of the housing such that, when the trigger is actuated, the force of the trigger overcomes the engagement with the housing portion whereby the plate pivots extremely rapidly through the operating position to the post-operating position.

6. The device of claim 5 wherein the relative size and shape of the retaining element and the housing portion is such as to prevent the retaining element from returning to the operating position after reaching the post-operating position.

7. The device of claim 1 further comprising a movable retaining element in engagement with the trigger to prevent the plate from being pivoted out of the pre-operating position.

8. The device of claim 7 wherein the movable retaining element comprises a pivotable element.

9. The device of claim 7 wherein the movable retaining element comprises a sheath.

10. The device of claim 7 wherein the movable retaining element comprises a removable cover over the trigger.

11. The device of claim 7, wherein the movable retaining element is a rotatable plate, rotatable about an edge of the housing to contact the trigger so that it may not be depressed.

* * * * *